US00PP13159P2

(12) United States Plant Patent
Saul

(10) Patent No.: US PP13,159 P2
(45) Date of Patent: Oct. 29, 2002

(54) DIANTHUS PLANT NAMED 'BEWITCHED'

(76) Inventor: Richard Gregg Saul, 308 Hester Valley Rd., Cleveland, GA (US) 30528

( * ) Notice: Subject to any disclaimer, the term of this patent is extended or adjusted under 35 U.S.C. 154(b) by 60 days.

(21) Appl. No.: 09/887,105

(22) Filed: Jun. 25, 2001

(51) Int. Cl.[7] ..... A01H 5/00
(52) U.S. Cl. ..... Plt./272

(58) Field of Search ..... Plt./281, 272

*Primary Examiner*—Kent L. Bell
(74) *Attorney, Agent, or Firm*—C. A. Whealy

(57) ABSTRACT

A distinct cultivar of Dianthus plant named 'Bewitched', characterized by its compact, mounded and low-growing plant habit; freely basal branching habit; light blue green-colored foliage; numerous light pink-colored flowers with central purple ring; and long flowering period.

1 Drawing Sheet

BOTANICAL CLASSIFICATION/CULTIVAR DESIGNATION

*Dianthus gracilis* cultivar 'Bewitched'.

BACKGROUND OF THE INVENTION

The present invention relates to a new and distinct cultivar of Dianthus plant, botanically known as *Dianthus gracilis* and hereinafter referred to by the name 'Bewitched'.

The new Dianthus is a naturally-occurring branch mutation of the *Dianthus gracilis* cultivar 'Firewitch', not patented. The new Dianthus was discovered by the Inventor in a controlled environment in Dahlonega, Ga. in June, 1999.

Asexual reproduction of the new Dianthus by vegetative stem cuttings taken in a controlled environment in Chamblee, Ga., has shown that the unique features of this new Dianthus are stable and reproduced true to type in successive generations.

SUMMARY OF THE INVENTION

The cultivar 'Bewitched' has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Bewitched'. These characteristics in combination distinguish 'Bewitched' as a new and distinct cultivar:

1. Compact, mounded and low-growing plant habit.

2. Freely basal branching habit.

3. Light blue green-colored foliage.

4. Numerous light pink-colored flowers with central purple ring.

5. Long flowering period.

Plants of the new Dianthus can be compared to plants of the parent, the cultivar 'Firewitch'. In side-by-side comparisons conducted in Atlanta, Ga., plants of the new Dianthus and the cultivar 'Firewitch' differ in the following characteristics:

1. Plants of the new Dianthus have a more rapid growth rate than plants of the cultivar 'Firewitch'.

2. Plants of the new Dianthus flower for a longer period of time than plants of the cultivar 'Firewitch'.

3. Flowers of plants of the new Dianthus are light pink with a central purple ring whereas flowers of plants of the cultivar 'Firewitch' are solid purple in color.

BRIEF DESCRIPTION OF THE PHOTOGRAPH

The accompanying colored photograph illustrates the overall appearance of the new Dianthus, showing the colors as true as it is reasonably possible to obtain in colored reproductions of this type. Colors in the photograph may differ slightly from the color values cited in the detailed botanical description which accurately describe the colors of the new Dianthus.

The photograph comprises a top perspective view of a one year-old flowering plant of 'Bewitched' grown in a garden.

DETAILED BOTANICAL DESCRIPTION

In the following description, color references are made to The Royal Horticultural Society Colour Chart except where general terms of ordinary dictionary significiance are used. The following observations and measurements describe plants grown in Atlanta, Ga., under conditions which approximate commercial practice in an unshaded outdoor nursery. During the production of the plants, day temperatures ranged from 50 to 95° F. and night temperatures ranged from 30 to 80° F. Measurements and numerical values represent averages of one year-old flowering plants grown in 1-liter containers. Measurements and color values were taken on plants during the spring.

Parentage: Naturally-occurring branch mutation of *Dianthus gracilis* cultivar 'Firewitch', not patented.

Propagation:

*Type.*—By vegetative stem cuttings.

*Time to initiate roots.*—Summer: About 10 days at 85° F. Winter: About 14 days at 65° F.

*Time to produce a rooted cutting.*—Summer: About 28 to 30 days at 85° F. Winter: About 45 days at 65° F.

*Root description.*—Fine, fibrous.

Plant description:

*Plant habit.*—Compact, mounded and low-growing.

*Growth habit.*—Freely basal branching; when pinched, lateral shoots potentially develop at every node.

*Plant height.*—About 12.5 cm.

*Plant width.*—About 23.5 cm.

*Lateral branch description.*—Length: About 16.5 cm. Diameter: About 1.5 mm. Internode length: Very short, about 2.5 mm. Strength: Strong. Texture: Glabrous, covered with waxy bloom. Color: Overall tonality, light blue-green; 146A covered with bloom, close to 122C.

*Foliage description.*—Arrangement: Leaves simple; symmetrical; abundant; opposite; sessile and decurrent. Length: About 2.7 cm. Width: About 2.5 mm. Shape: Linear. Apex: Sharply acute. Margin: Entire with ciliation. Texture, upper and lower surfaces: Glabrous, covered with waxy bloom. Venation pattern: Parallel, linear. Color: Young and mature foliage, upper surface: Overall tonality, light blue-green; close to 147A covered with waxy bloom, close to 122C. Young and mature foliage, lower surface: Overall tonality, light blue-green; close to 146A to 147A covered with waxy bloom, close to 122C. Venation, upper surface: Close to 147A. Venation, lower surface: Close to 146A.

Flowering description:

*Appearance.*—Single rounded flowers that face upright. One flower per lateral branch; freely flowering, usually about 40 to 50 flowers per plant.

*Flowering response.*—Long flowering period, plants flower from spring through summer in Georgia.

*Postproduction longevity.*—Flowers last about 4 to 7 days on the plant depending on environmental conditions. Flowers persistent.

*Fragrance.*—Moderately fragrant; spicy, clove-like.

*Flower size.*—Diameter: About 2.9 cm. Depth (height): About 2.3 cm.

*Flower buds.*—Length: About 1.7 cm. Diameter: About 3 mm. Shape: Tubular, elongated. Color: 146A, overlain with anthocyanin, close to 187A.

*Petals/petaloids.*—Quantity: Five in a single whorl. Length: About 2.8 cm. Width: About 1.4 cm. Shape: Roughly spatulate or fan-shaped, tapering towards base. Apex: Rounded, emarginate. Base: Attenuate. Margin: Finely serrated giving a fringed appearance. Texture: Velvety, smooth; sparse pubescence on upper surface; lower surface, glabrous. Color: When opening, upper surface: Ground color, close to 155D, overlain with 70B; spots towards center forming a ring, more saturated than 71A; base and tube, 145C to 145D. When opening, lower surface: Ground color, close to 155D, faintly underlain with 70B; base and throat, 145C to 145D. Fully opened, upper surface: Ground color, close to 155D, overlain with 70B; spots towards center forming a ring, more saturated than 71A; base and tube, 145D, towards apex of tube, 155D. Fully opened, lower surface: Ground color, close to 155D, faintly underlain with 70B; base and throat, 145D, towards apex of throat, 155D.

*Sepals.*—Quantity: Five. Calyx length: About 1.8 cm. Calyx diameter: About 3.5 mm. Calyx shape: Tubular. elongate. Apex: Acute. Texture: Smooth, glabrous. Color: Upper surface: 144A. Lower surface: 146A overlain with anthocyanin, close to 187A, at apices and towards base.

*Peduncles.*—Length: About 3.1 cm. Diameter: About 1 mm. Aspect: Upright. Strength: Strong. Color: 146A, covered with waxy bloom, close to 122A.

*Reproductive organs.*—Androecium: Stamen number: About 10. Filament length: About 2.1 cm. Filament diameter: Less than 1 mm. Filament color: 155D. Anther size: About 1.5 mm by 1 mm. Anther shape: Roughly oblong. Anther color: Close to 15A. Pollen: Scarce. Pollen color: Close to 10D. Gynoecium: Pistil quantity: Two. Pistil length: About 1.2 cm. Style length: About 7 mm. Style diameter: Less than 1 mm. Style color: 155D. Stigma shape: Linear, recurved. Stigma color: 155D. Ovary color: 144A.

*Fruit.*—Length: About 2.7 cm. Diameter: About 4 mm. Texture: Smooth with four longitudinal sutures. Color: 146A.

*Seed.*—Quantity: About 17 per fruit. Length: About 3.5 mm. Diameter: About 3 mm. Shape: Roughly ovate to oblong, flattened. Color: Close to 162A.

Disease resistance: Plants of the new Dianthus have not been observed to be resistant to pathogens common to Dianthus.

It is claimed:

1. A new and distinct cultivar of Dianthus plant named 'Bewitched', as illustrated and described.

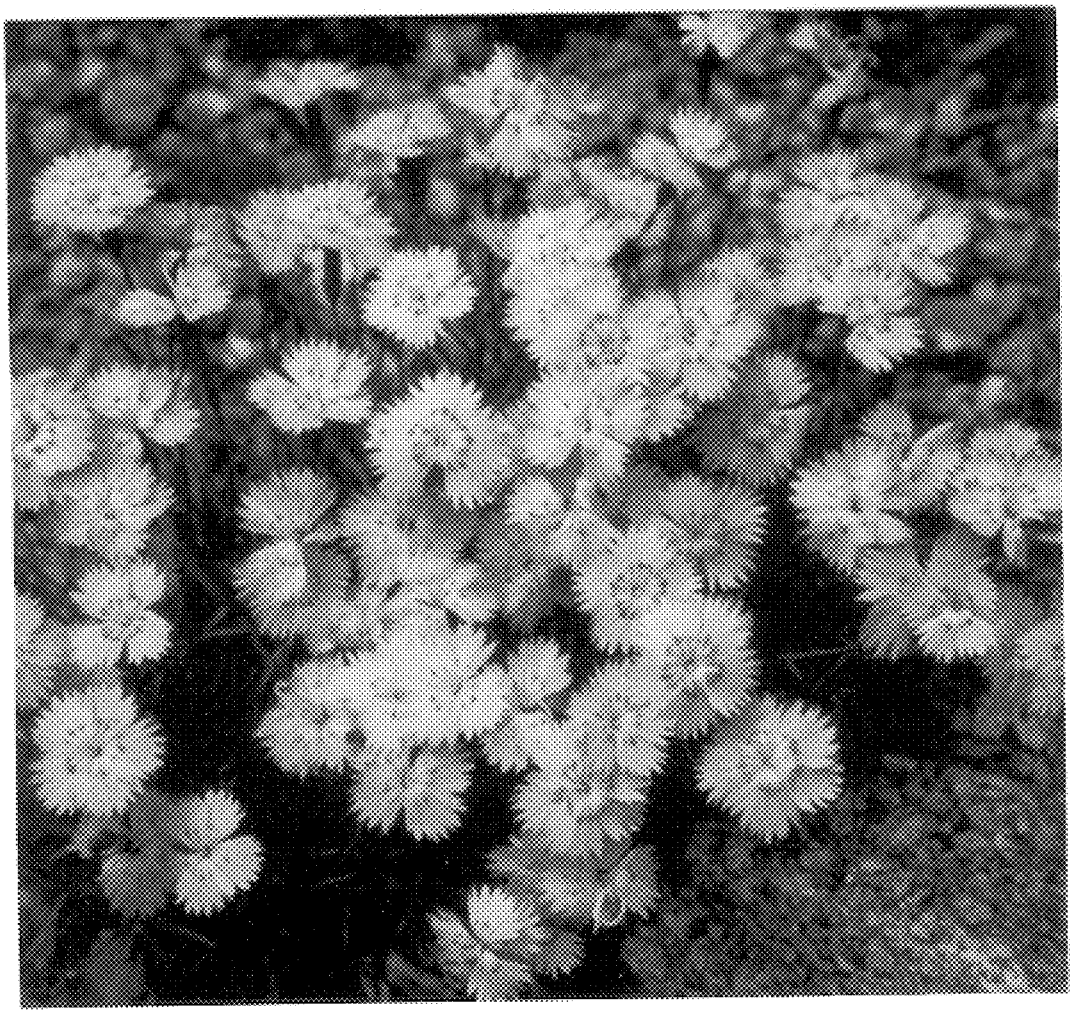

* * * * *